United States Patent
Rennich

(10) Patent No.: US 6,960,218 B2
(45) Date of Patent: Nov. 1, 2005

(54) EXTERNAL INCONTINENCE CLAMP

(76) Inventor: Henry Rennich, 23 Scandia Point NW., Calgary, Alberta (CA), T3L 1T6

(*) Notice: Subject to any disclaimer, the term of this patent is extended or adjusted under 35 U.S.C. 154(b) by 0 days.

(21) Appl. No.: 10/688,053

(22) Filed: Oct. 20, 2003

(65) Prior Publication Data
US 2005/0085835 A1 Apr. 21, 2005

(51) Int. Cl.$^7$ ............................. A61B 17/04; A61F 6/02
(52) U.S. Cl. ....................... 606/151; 128/843; 606/157
(58) Field of Search ................................. 606/151, 157, 606/843

(56) References Cited

U.S. PATENT DOCUMENTS

| | | | |
|---|---|---|---|
| 3,147,754 A | | 9/1964 | Koessler |
| 3,766,926 A | * | 10/1973 | Bliss ............................ 606/151 |
| 4,275,813 A | * | 6/1981 | Noiles ........................... 206/339 |
| 4,458,681 A | * | 7/1984 | Hopkins ........................ 606/157 |
| 4,942,886 A | | 7/1990 | Timmons |
| 5,336,157 A | * | 8/1994 | Hale ............................. 600/41 |
| 5,571,125 A | * | 11/1996 | Chadwick ..................... 606/157 |
| 5,620,452 A | * | 4/1997 | Yoon ............................ 606/151 |
| 6,007,552 A | * | 12/1999 | Fogarty et al. ............... 606/157 |
| 2004/0059354 A1 | * | 3/2004 | Smith et al. .................. 606/151 |

FOREIGN PATENT DOCUMENTS

FR 2598905 * 11/1987 .................. 606/151

* cited by examiner

Primary Examiner—Gary Jackson

(57) ABSTRACT

An external incontinence clamp for stopping involuntary voiding of urine is provided. The clamp includes a first rigid member having opposed ends, each end defining a passage extending therethrough, a second rigid member having opposed ends, each end defining a passage extending therethrough, and two pins of generally u-shape. The pins are adapted to be received by the passages defined by the ends of the first rigid member and of the second rigid member so as to secure the first rigid member in a spaced and generally parallel relationship to the second rigid member. The penis is positioned between the first and second members so that the underside of the penis is in contact with the second member and the top surface of the penis is in contact with the first member, thereby stopping involuntary voiding of urine. A clamp kit includes a plurality of pins of different width to vary the force applied to the penis.

13 Claims, 2 Drawing Sheets

EXTERNAL INCONTINENCE CLAMP

BACKGROUND OF THE INVENTION

1. Field of the Invention

The present invention relates generally to male incontinency devices. More particularly, relating to an external incontinency device that is clamped to a male's penis to restrict urine flow through the urethra.

2. Description of the Prior Art

Due to the anatomy of a penis, external devices that are clamped or other wise secured to a penis can be very effective in controlling urine flow through the urethra. The urethra is a passageway through which urine travels and it is located on the under side of the penis relatively close to the skin surface. A very small amount of pressure applied to the urethra will collapse the passageway and prevent urine from flowing through. There are many know prior art devices that attempt to accomplish this to control or prevent involuntary voiding of a bladder or to prevent urine leakage.

An example of an aforementioned device is disclosed in U.S. Pat. No. 4,942,866 to Timmons. This patent discloses an external incontinency clamp having two arcuate members hinged together at one end and a releasable fastener on the opposite ends, which are adapted to receive and clamp a penis therebetween.

Similarly, U.S. Pat. No. 3,147,754 to Koessler discloses a device for controlling incontinence having a U-shaped part with a cooperating cross bar, which together serve as a clamp for a penis.

Lastly, U.S. Pat. No. 5,571,125 to Chadwick discloses a penis-clamping device including a cushioned clamp that is hinged at one end and provided with an adjustable tensioning closure device at its other end.

While the above-described devices fulfill their respective, particular objectives and requirements, the aforementioned patents do not describe an external incontinence clamp for applying an equal force across a penis to prevent the penis from slipping towards either side of a centerline of the clamp, thereby preventing inadvertent opening of the urethra causing urine leakage.

Therefore, a need exists for a new and improved external incontinence clamp that can be used for preventing involuntary voiding of a bladder by restricting urine flow through the urethra. In this regard, the present invention substantially fulfills this need. In this respect, the external incontinence clamp according to the present invention substantially departs from the conventional concepts and designs of the prior art.

SUMMARY OF THE INVENTION

In accordance with the present invention, an external incontinence clamp is provided. The clamp includes a first rigid member having opposed ends, each end defining a passage extending therethrough, a second rigid member having opposed ends, each end defining a passage extending therethrough, and two pins of generally u-shape. The pins are adapted to be received by the passages defined by the ends of the first rigid member and of the second rigid member so as to secure the first rigid member in a spaced and generally parallel relationship to the second rigid member.

In another embodiment, an external incontinence clamp for attachment to a penis for stopping involuntary voiding of urine through the urethra passage of the penis is provided. The clamp includes a first rigid member having opposed ends, each end defining a passage extending therethrough, a second rigid member having opposed ends, each end defining a passage extending therethrough, and two pins of generally u-shape. The pins are adapted to be received by the passages defined by the ends of the first rigid member and of the second rigid member so as to secure the first rigid member in a spaced and generally parallel relationship to the second rigid member. The first and second rigid members having a length of at least the width of the penis and each member includes a pad for increasing wearing comfort.

In another aspect of the invention, using pins with different widths varies the force applied to the penis. Preferably a kit is providing that includes the clamp and pins having different widths to vary the force applied to the penis.

There has thus been outlined, rather broadly, the more important features of the invention in order that the detailed description thereof that follows may be better understood and in order that the present contribution to the art may be better appreciated.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

An object of the present invention is to provide an external incontinence clamp for stopping involuntary voiding of urine through a penis.

Another object of the present invention is to provide an external incontinence clamp that eliminates slipping of the penis to either side of the clamp to prevent the clamp from failing to stop involuntary voiding of urine through a penis.

Still a further object of the present invention is to provide an external incontinence clamp that is easy to operate and does not require removal of the clamp for urination.

Yet an additional object of the present invention is to provide an external incontinence clamp kit.

Lastly, it is an object of the present invention to provide an external incontinence clamp and method of operating the same that has a low cost of manufacture with regard to both materials and labor, and which accordingly is then susceptible of low prices of sale to the consuming public, thereby making such clamp economically available to the buying public.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DETAILED DESCRIPTION OF THE INVENTION

Figure 1:
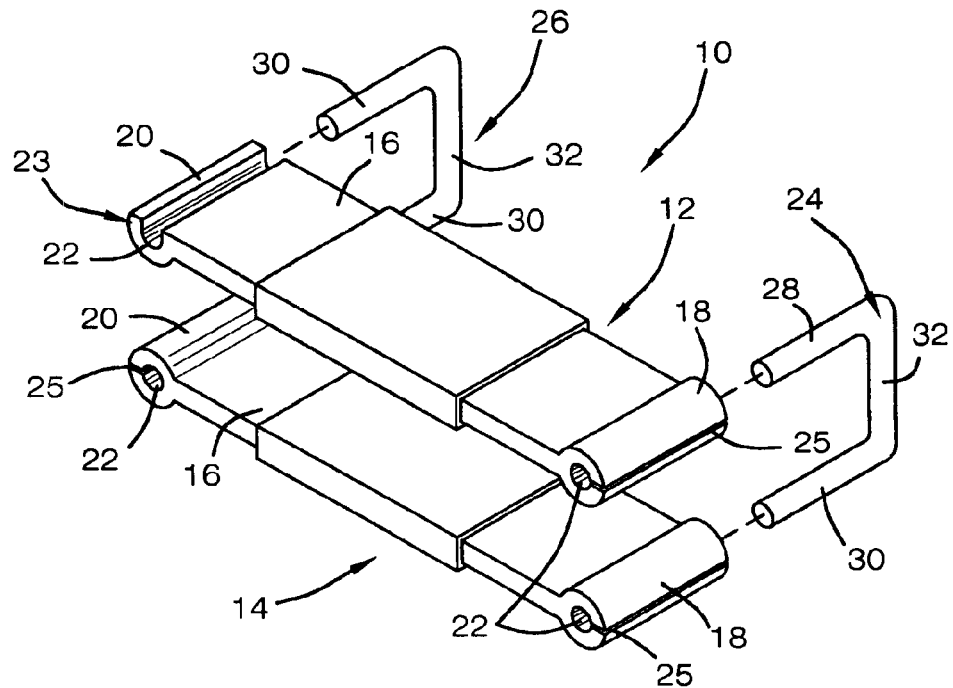
FIG. 1 is a perspective view of the preferred embodiment of the external incontinence clamp constructed in accordance with the principles of the present invention.

Referring now to the drawings, and particularly to FIGS. 1–5, a preferred embodiment of the external incontinence clamp of the present invention is shown and generally designated by the reference numeral 10.

In FIG. 1, a new and improved external incontinence clamp 10 of the present invention for preventing involuntary voiding of a bladder by restricting urine flow through the urethra of a penis is illustrated and will be described. More particularly, the external incontinence clamp 10 includes a first clamping member 12 and a second clamping member 14, which are rigid and generally rectangular shape and which are coupled together in a spaced relationship by generally U-shaped connection pins 24 and 26. Each member 12 and 14 have a mid portion 16 and two ends 18 and 20. The mid portion 16 is integral with and extends between the two ends 18 and 20. Preferably, the mid portion 16 of each member 12 and 14 is substantially rectangular in shape and is rigid.

Each end 18 and 20 includes a through passage 22 that is formed along the width thereof and perpendicularly to the mid portion 16. Each passage 22 is adapted for frictionally receiving the pins 24 and 26. Preferably, the passages 22 have a circular cross-section. The ends 18 and 20 are generally cylindrically shaped and am diametrically larger than the thickness of the mid portion 16. The end 20 of the first member 12 further includes a slot 23 which formed through the end and along the the passage 22. The width of the slot 23 is substantially equal to the diameter of the passage 22. The ends 18 and 20 of the second member 14 and the end 18 of the first member 12 each include a slit 25 which is formed transversely across each of the ends from the exterior surface to the passage 22. The slits 25 allow the ends 18 and 20 to expand slightly when the pins 24 or 26 are passed through the passages 22.

The pins 24 and 26 each includes a bridge 32 and two legs 28 and 30 that extend from the bridge and substantially parallel to each other. The legs 28 and 30 may be of equal or of different lengths and are adapted to be frictionally received by the passages 22. Upon inserting the pins 24 and 26 into the passages 22 of the ends 18 and 20 of the first and second clamping members 12 and 14, the members are secured together in a spaced relationship with the mid portions 16 of each clamping member being substantially parallel and with their respective ends at a fixed, spaced distance from each other.

The pins 24 and 26 are preferably stainless steel. However, one skilled in the art will appreciate that the pins may be of other materials while still retaining the desired function of the pins without departing from the spirit and scope of the present invention. The first clamping member 12 and the second clamping member 14 can be constructed from any material that affords rigidity to the members and is also hypoallergenic and non-irritating to the skin. Preferably, the first and second members 12 and 14 are constructed from Polyvinyl chloride (PVC).

Figure 2:
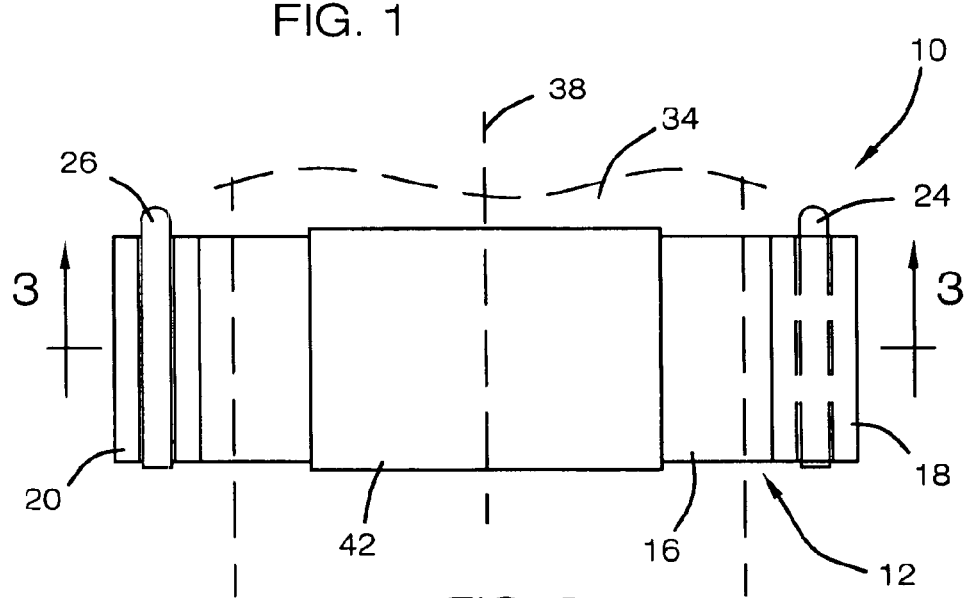
FIG. 2 is a top plan view of the external incontinence clamp of the present invention.
Figure 3:
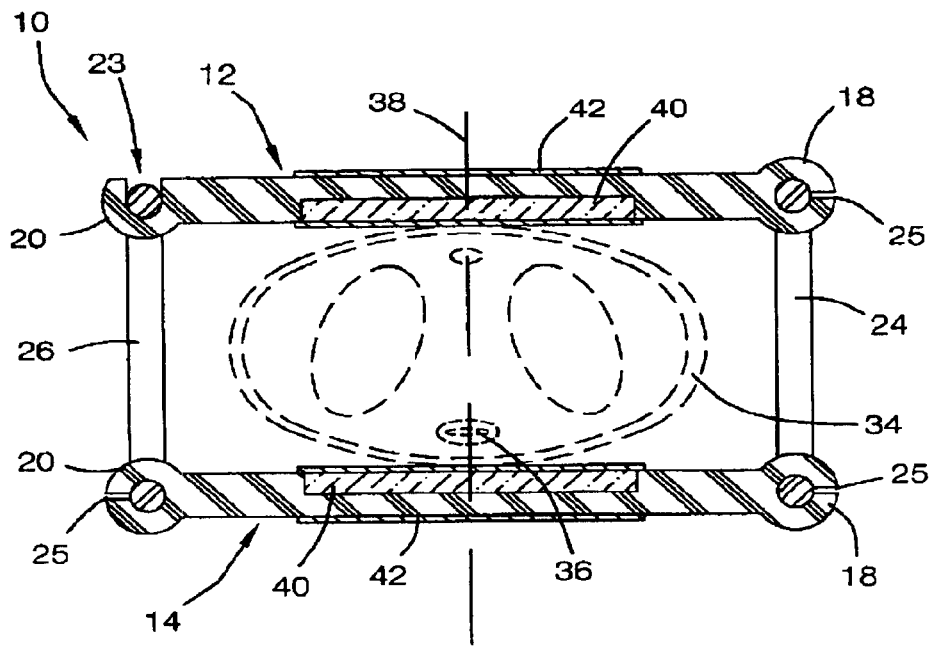
FIG. 3 is a sectional view taken along line 3—3 in FIG. 2 of the external incontinence clamp of the present invention.

Now turning to FIGS. 2 and 3, the new and improved external incontinence clamp 10 of the present invention is illustrated in use positioned on a penis 34. The penis 34 is drawn in broke-line and only a portion thereof is illustrated. The portion of the penis illustrated is a section towards the glans thereof. The penis 34 is positioned and clamped between the first clamping member 12 and the second clamping member 14 to apply pressure to the urethra passage 36, thereby preventing urine from being discharged through the penis. For the clamp 10 to properly function, the center of the urethra passage 36 must be placed as close as possible to a centerline 38 of the clamp. The clamp 10, applies an equal force along the portion of the penis 34 that is in contact with the mid portions 16, thereby minimizing penis slippage to either side of the clamp.

Figure 4:
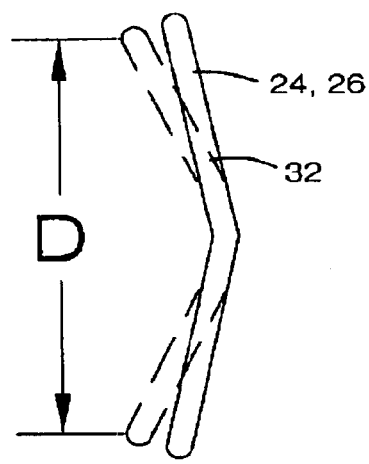
FIG. 4 is a back elevation view of an alternate embodiment of a connection pin of the present invention.
Figure 5:
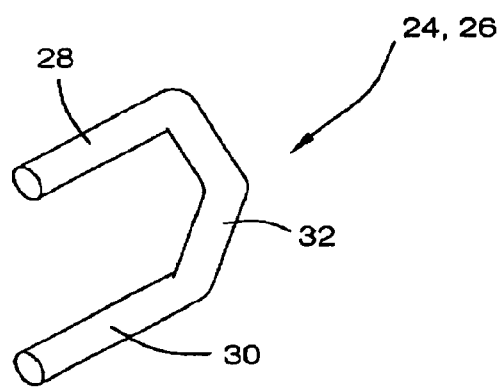
FIG. 5 is a perspective view of the connection pin shown in FIG. 4.

The amount of force applied by the clamp 10 to the penis 34 can be adjusted by varying the length of the bridge 32 of the pins 24 and 26, thereby varying the distance between the legs and between the mid portions 16. Reducing the length of the bridge 32 increases the applied force while increasing the length reduces the applied force. The length of the bridge 32 of the each pin 24 and 26 must be substantially equal so that an equal force is applied to either side of the clamped portion of the penis. The legs 28 and 30 of the pins define a space between the inner facing sides thereof. The bridge 32 can be of a length so that the defined space between the legs is at least about 0.5 inches, preferably from about 0.5 inches to about 0.75 inches. Referring to FIGS. 4 and 5, in an alternate embodiment, the pins 24 and 26 can have a bridge 32 that is slightly bent at a mid point thereof. A user to either increase or decrease the amount of applied force to the penis by the clamp 10 can adjust the degree of the bend of the bridge 32, thereby increasing or decreasing the distance D between the legs of the pin. By increasing the bend degree, the applied force is increased and reducing the bend degree, the force is decreased.

In an additional embodiment, the mid portion 16 of each member 12 and 14 can be formed with a recess for receiving a pad 40 for increasing wearing comfort. A removable sleeve 42 is provided for covering the pad 40 to prevent soiling thereof. Preferably, the pad 40 is closed cell non-liquid foam and the sleeve 42 is constructed from a non-chaffing elastomeric material.

The read portions 16 of first and second clamping members 12 and 14 are of a length that is at least equal to the width of the penis 34. Preferably, the length of the mid portions 16 is slightly greater than the width of the penis 34 so that the ends 18 and 20 of the first and second clamping members 12 and 14 remain free from contact with the penis, thereby allowing enough space on either side of the penis to ensure proper blood circulation through the penis.

To postilion the clamp 10 on the penis 34, the first and second clamping members 12 and 14 may be initially secured together by inserting a pin 24 into the passages 22 defined by the ends 18 of the first and second members. At this point, one leg of the remaining pin 26 maybe inserted to the passage 22 defined by the end 20 of the second member 14. The penis 34 is then positioned between the first and second members, towards the glans of the penis, so that the urethra passage 36 is in close proximity to the centerline 38 of the clamp. Once the penis 34 is correctly positioned, the free leg of pin 26 is then passed through the slot 23 and frictionally snapped into the passage 22 of the end 20 of the first member 12 locking the clamp in position. To pass urine, the user simply unlocks the clamp by removing the leg of the pin 26 snapped into the slotted passage 22 of the first member 12. After urination, the user simply relocks the clamp in position by once again snapping the pin 26 back into the passage 22 of the end 20 of the first member 12.

In an additional embodiment, and for user convenience, a kit is provided having a clamp 10 including the first rigid member 12, the second rigid member 14, and a plurality of pairs of pins. At least two pairs of pins are provided where each pair of pins have different bridge length than die other pain of pins so that a user may select a pair which provides the correct applied force to the penis. Preferably one pair has a bridge length so the defined space between the legs of the pins is about 0.5 inches, the second pair about 0.625 inches and the third pair about 0.75 inches.

While a preferred embodiment of the external incontinence clamp has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An external incontinence clamp that is removably attachable to a penis for selectively controlling the discharge of urine through the penis, the incontinence clamp comprising:

a pair of clamping members each having opposed ends and a mid portion extending between the opposed ends, said pair of clamping members being arrangable generally parallel and about said penis with said opposed ends extendable past the width of said penis and with said mid portion of each clamping member contactable with said penis, each of said opposed ends of each clamping member of said pair of clamping members includes a passage way which extends therethrough along the width of said end;

a pair of pins, each pin of said pair of pins includes two legs extending from a bridge portion to generally define a U-shaped pin; and wherein said legs of said pins are frictionally received by said passages to secure said pair of clamping members at said opposed ends and in a generally parallel and spaced distance about said penis, thereby applying a predetermined clamping force to said penis to prevent the passage of urine therethrough, and one of said pins being selectively disengaged from one clamping member to allow the passage of urine through said penis and then being reengaged to prevent passage of urine.

2. The external incontinence clamp as recited in claim 1, wherein one opposed end of one of said pair of clamping members includes a slot formed through said opposed end along said passage way thereof; and further wherein one of said pins is selectively disengaged from said clamping member by removing one leg of said pin from said opposed end through said slot.

3. The external incontinence clamp as recited in claim 2, further comprising:

a pad positioned about each of said mid portions of said pair of clamping members.

4. The external incontinence clamp as recited in claim 2, wherein said bridge of each of said pair of pins is bent at a mid point thereof.

5. The external incontinence clamp as recited in claim 4, wherein the degree of said bend of each bridge portion is adjustable to control the amount of said clamping forced applied to said penis.

6. The external incontinence clamp as recited in claim 1, wherein each of said pair of clamping members are rigid.

7. The external incontinence clamp as recited in claim 1, wherein said penis is not punctured or pierced by said clamp.

8. A male incontinence clamp for temporary attachment to a penis for selectively controlling the discharge of urine through the penis, the incontinence clamp comprising:

a pair of clamping members each having opposed ends and a mid portion extending between the opposed ends, said pair of clamping members being arrangable generally parallel and about said penis with said opposed ends extendable past the width of said penis and with said mid portion of each clamping member contactable with said penis, each of said opposed ends of each clamping member of said pair of clamping members includes a passage way which extends therethrough along the width of said end;

a pair of pins, wherein each pin of said pair of pins includes two legs extending from a bridge portion to generally define a U-shaped pin; and and wherein said legs of said pins are frictionally received by said passages to secured said pair of clamping members at said opposed ends and in a generally parallel and spaced distance about said penis.

9. The incontinence clamp as recited in claim 8, further comprising:

a pad positioned about each of said mid portions of said pair of clamping members.

10. The incontinence clamp as recited in claim 8, wherein each of said pair of clamping members are rigid.

11. The incontinence clamp as recited in claim 8, wherein one opposed end of one of said pair of clamping members includes a slot formed through said opposed end along said passage way thereof; and further wherein one of said pins is selectively disengaged from said clamping member by removing one leg of said pin from said opposed end through said slot.

12. The incontinence clamp as recited in claim 11, wherein said bridge of each of said pair of pins is bent at a mid point thereof; and the degree of said bend of each bridge portion is adjustable to control the amount of said clamping forced applied to said penis.

13. The incontinence clamp as recited in claim 8, wherein the length of each of said pair of clamping members is sufficient so that said opposed ends of said clamping members are free from contact with said penis.

* * * * *